United States Patent [19]

Cromer

[11] 4,322,278
[45] Mar. 30, 1982

[54] GAS DETECTION UNIT

[75] Inventor: Raymond B. Cromer, New York, N.Y.

[73] Assignee: Becton, Dickinson and Company, Paramus, N.J.

[21] Appl. No.: 170,367

[22] Filed: Jul. 21, 1980

[51] Int. Cl.³ .................. G01N 27/28; G01N 27/54
[52] U.S. Cl. .............................................. 204/195 R
[58] Field of Search .................. 525/301; 204/195 R, 204/1 N; 8/DIG. 9; 428/280

[56] References Cited

U.S. PATENT DOCUMENTS

| | | | |
|---|---|---|---|
| 3,177,269 | 4/1965 | Nowak et al. | 8/DIG. 9 X |
| 3,284,541 | 11/1966 | Stanton et al. | 8/DIG. 9 X |
| 3,776,832 | 12/1973 | Oswin et al. | 204/195 R |
| 3,824,167 | 7/1974 | Oswin et al. | 204/195 R |
| 3,849,201 | 11/1974 | Kordesch | 204/195 R X |
| 3,909,386 | 9/1975 | Oswin et al. | 204/195 R |
| 3,992,267 | 11/1976 | Oswin et al. | 204/1 T |

FOREIGN PATENT DOCUMENTS 843190 8/1960 United Kingdom ................ 525/301
1025474 4/1966 United Kingdom ................ 525/301

Primary Examiner—G. L. Kaplan

[57] ABSTRACT

A wick system for a hydrazine gas detection cell is provided to enhance and sustain the connection between the electrodes of the cell. The wick system of the invention absorbs the electrolyte which may be potassium hyroxide, for example, and by capillary action provides a continuous electrolyte path between the electrodes. The wick may be in the form of a flat piece extending in one plane for those cells having all electrodes positioned at one end thereof. Alternatively, the wick may be substantially tubular to extend from one end of a cylindrical electrolyte containing chamber to another, for a cell having electrodes positioned at each end thereof. Additionally, the wick may extend from one end of the cell to the other in a folded bellows-like form. The wick system is comprised of a material which withstands the alkaline environment of the required electrolyte, while at the same time providing the proper wetting action to provide a continuous electrolyte path between the electrodes.

4 Claims, 3 Drawing Figures

GAS DETECTION UNIT

BACKGROUND OF THE INVENTION

This invention relates generally to an electrochemical cell for use in a gas detector unit. More particularly, this invention relates to a wick system useful in the functioning of a cell for detecting monomethylhydrazine, in that it provides for continuous and enhanced contact between the electrodes of the cell. The wick is comprised of a wettable material which absorbs electrolyte, and by capillary action maintains the continuous contact. Thus, as the gas detector unit is used over a period of time and the quantity of electrolyte diminishes, the cell will still operate because the wick continues to absorb and carry the electrolyte to the electrodes and maintains a continuous path between them. Moreover, the wick of the invention utilizes the internal vapor pressure of the electrolyte and will compensate for any water loss in those instances where an aqueous electrolyte system is being utilized.

This invention is an improvement over the inventions described in U.S. Pat. Nos. 3,992,267, issued Nov. 16, 1976; 3,824,167, issued July 16, 1974; 3,776,832, issued Dec. 4, 1973 and 3,909,386, issued Sept. 30, 1975. Each of these patents is incorporated by reference in its entirety herein. In addition, this invention is related to the invention disclosed in co-pending application Ser. No. 170,368 filed simultaneously herewith.

In the past, most electrochemical gas sensors utilizing a liquid electrolyte could only be used when maintained in one stabilized position. The sensor had to be oriented so as to make sure that all of the electrodes were in continuous contact with the electrolyte. As will be appreciated, the sensors of the past, subject to these limitations, were not properly operable in conditions where large amplitude vibrations might be present. Such vibrations, as will be understood, can momentarily isolate one or more of the electrodes from the electrolyte causing surges in the sensor response. Attempts to overcome these problems include utilizing a packing filling the entire content of the electrolyte cavity. While such a system provides a continuous contact between the electrodes, it reduces the quantity of electrolyte which may be introduced into a sensor of any given size, and because of the high absorbent qualities of the packing, it tends to disperse the electrolyte more or less uniformly throughout the cavity or container for the electrolyte. In the case of an aqueous electrolyte, such dispersed electrolyte will tend to degrade sensor performance as the sensor loses water by evaporation to dry sampled gas. Also, a small shrinkage in the volume of the packing will cause it to pull away from one or more of the electrodes and cause the sensor to cease functioning.

By contrast, the present invention through the use of the wick system, effectively provides appropriate contact on a continuous basis between the electrodes without excessively dispersing the electrolyte. Moreover, the electrochemical sensor, incorporating the invention herein is independent of its attitude and is not affected by environmental conditions such as excessive vibration or movement during the functioning thereof.

In sensors for use in determining the presence of hydrazine, potassium hydroxide may be used as the electrolyte. It has been determined, in accordance with this invention, that polypropylene is useful as the wick material in this environment. That is, polypropylene will not degrade in the alkaline environment of the electrolyte. Because of the general hydrophobic character of polypropylene, it will not act effectively as a wick material. It has been discovered, however, in accordance with a further aspect of this invention that polypropylene grafted with hydrophilic groups will act in a highly effective manner as a wicking material.

DETAILED DESCRIPTION OF THE INVENTION

With the invention herein, a thin sheet of an electrolyte wettable modified polypropylene material is utilized, for example, in contact with all electrodes adjacent the electrolyte chamber. Satisfactory results have been achieved, in accordance herewith, and under satisfactorily and economically attractive conditions in commercial scale operations using a woven or nonwoven polypropylene cloth or a sintered polypropylene sheet comprised of particles of the thermoplastic sintered into such a sheet to provide the porous property required to give the capillary action desired between the electrodes. The polypropylene is modified to render it hydrophilic by the introduction of grafted hydrophilic groups. One such material is polypropylene with grafted methacrylic acid. The material will be relatively thin, as discussed above, and preferably within the range of between about 0.005 inches–0.150 inches.

Representative materials useful as the wick material herein include Permion E1243, a non-woven polypropylene felt with grafted methacrylic acid groups, manufactured by R.A.I. Corporation, Hauppauge, N.Y.; a polypropylene filter cloth, manufactured by Aldrich Chemical Company, Milwaukee, Wis.; and Porex, a sintered polypropylene manufactured by Glasrock Products, Inc., Fairburn, GA. It will be appreciated that other polymeric materials may be used as long as they possess the property of non-degradability in the alkaline environment, and are hydrophilic.

The form of the wick may be of a variety of configurations depending upon the configuration of the sensor itself. For example, some sensors provide for the positioning of the electrodes all at one end of the electrolyte cell and generally in a single plane. With this arrangement, the wick of the invention will be flat and also in one plane and positioned adjacent to the electrodes involved. For the gas detector unit, in accordance herewith, it is preferable to utilize three electrodes, including a working electrode (the anode), a counterelectrode (the cathode) and a reference electrode, as discussed in U.S. Pat. No. 3,776,832. The third or reference electrode is utilized to maintain a fixed relative potential between the anode and the reference electrode, as described in U.S. Pat. No. 3,776,832.

In some configurations of gas detection units, the units are configured to provide the anode at one end of an electrolyte chamber and the cathode and reference electrode at the opposite end. In those instances where such a configuration is utilized, it is necessary to provide a wick configuration which will extend from one end of the electrolyte chamber to the opposite end. Such electrolyte configurations include a wick extending from one end of the chamber to the opposite end. It may be tubular for a cylindrical chamber, with the wick extending along the walls of the chamber from one end to the other and comprised of, for example, a molded sintered polypropylene sheeting material as discussed above with a portion extending along an electrode at each end of the chamber. The sintered material may be heat sealed for appropriate contact with the electrodes. A further configuration may be in the form of a folded bellows-shaped flat piece of polypropylene felt material as discussed above extending from one end of the chamber to the opposite end and heat sealed at either end for fixed contact. Such an arrangement provides for efficient contact of the electrolyte in the chamber along its entire extent and causes the wick to carry the electrolyte material by capillary action to the electrodes involved. Such a "bridging wick" need not adhere to the inside surface of the sensor electrolyte chamber, but should be long enough to contain one or more folds so as to maintain contact with the electrolyte, and avoid pulling away from the electrodes.

As discussed above, in any one of the forms described for the wick of the invention, the wicking material need not remain in continuous contact with the bulk of the electrolyte. Once the electrodes and wick have been thoroughly wetted by the electrolyte, the internal vapor pressure of the electrolyte will more than compensate for any water loss to the environment through the electrodes during use of the sensor unit.

With the foregoing and additional objects in view, this invention will now be described in more detail, and other objects and advantages thereof will be apparent from the following description, the accompanying drawings, and the appended claims.

Figure 1:
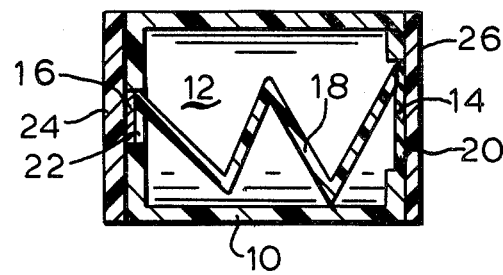
FIG. 1 is a longitudinal sectional view of an electrolyte chamber illustrating the invention in the form of a bridging wick extending from one end of the chamber to the opposite end.

Referring to the drawings in which like reference characters refer to like parts throughout the several views thereof, an embodiment of apparatus for practicing the invention is shown in the form of a tubular sensor unit 10 with an electrolyte chamber 12 which contains electrolyte for establishing an electrical connection between electrodes 14, 16 positioned at each end of the chamber. A wick 18 is shown in the form of a flat folded sheeting material with a portion 20 thereof extending along and heat sealed to electrode 14, and a portion 22, thereof extending along and heat sealed to electrode 16. As will be appreciated, chamber 12 is enclosed at each end by end plates 24, 26 and will have the appropriate electrical connections and provision for the introduction of a gas to be sensed by the cell adjacent electrode 16. Reference is made, in this connection, to the structure as generally shown in U.S. Pat. No. 3,909,386.

At any rate, with the embodiment shown in FIG. 1, a "bridging wick" is shown which extends from electrode 16 to electrode 14 positioned at each end of the chamber. As will be understood, there may be two electrodes in the form of a cathode and a reference electrode (not shown) at the position of electrode 14. In such a circumstance, the portion 20 of the wick 18 will extend as shown in FIG. 1 along and touch both electrodes.

Figure 2:
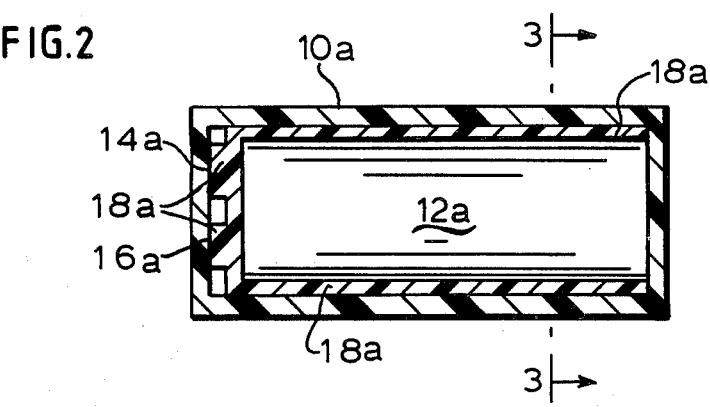
FIG. 2 is a longitudinal sectional view of a further embodiment of the invention illustrating the wick of the invention in cylindrical form.
Figure 3:
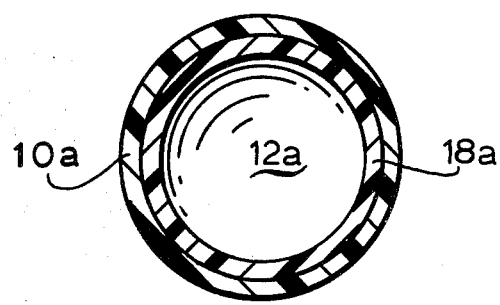
FIG. 3 is an enlarged cross-sectional view taken along line 3—3 of FIG. 2.

Referring now to FIGS. 2, and 3 the wick 18a shown is tubular in shape and extends along the cylindrical walls of electrolyte chamber 12a of sensor unit 10a. In this arrangement, the electrodes 14a, 16a are positioned at one end of electrolyte chamber 12a. The tubular wick, by extending along the entire length of the chamber, is exposed to the electrolyte at any portion of the length of the chamber and by capillary action carries the electrolyte to and adjacent each of the electrodes 14a, 16a positioned at one end of the chamber. Moreover, once the electrolyte has wetted the wick and the electrodes 14a, 16a, a proper contact is maintained by internal vapor pressure between the electrodes regardless of the amount of electrolyte remaining in the chamber. Again, as will be understood, there may be two electrodes in the form of a cathode and a reference electrode (not shown) at the position of electrode 14a.

Obviously, all of the above serves to make the methods and apparatus herein highly advantageous commercially because of the continuous utilization of whatever electrolyte content is available in the chamber by the wick system in accordance herewith. Moreover, the wick is impervious to and withstands degradation from the alkaline electrolyte, while at the same time providing the desired capillary action necessary in order to provide a proper signal.

While the methods and apparatus herein disclosed form preferred embodiments of this invention, this invention is not limited to those specific methods and apparatus, and changes can be made therein without departing from the scope of this invention, which is defined in the appended claims. For example, the wick need not be in the form of a folded bellows-like flat sheet but may be, for example, in helical form extending from one end of the sensor chamber to the other. Also, it may be desirable to form the molded sintered wick in the form of intermittent strips extending along the walls of the chamber as opposed to a solid cylindrical wick, if material costs are important, with the individual strips being joined to a single portion at one end of the chamber.

What is claimed is:

1. An electrochemical cell for detecting and measuring hydrazine in a gaseous medium containing hydrazine in as little as parts per billion; comprising
    (a) an electrolyte chamber containing an aqueous potassium hydroxide electrolyte;
    (b) an anode with one side facing said chamber;
    (c) a cathode with one side facing said chamber;
    (d) a reference electrode with one side facing said chamber;
    (e) means interconnecting said anode and said reference electrode for maintaining a preselected fixed reference potential on said anode;
    (f) intake means for exposing said anode to said gaseous medium for detecting hydrazine contained therein;
    the improvement characterized by
    (g) wick means contained entirely within said chamber and interconnecting said anode, said cathode and said reference electrode;
    (h) said wick means being substantially rigid and flat for continuously maintaining in non-sagging relationship firm engagement with the said surfaces of said anode, said cathode and said reference electrode facing said chamber;
    (i) said wick means extending along the entire length of said chamber for continuously carrying said electrolyte and the vapor pressure thereof to said anode, said cathode and said reference electrode;

(j) said wick means having a thickness within the range of between about 0.005 and 0.150 inches; and
(k) said wick means comprised of porous sintered polypropylene with grafted methacrylic acid groups thereon.

2. The apparatus of claim 1, further characterized by
(a) said chamber is cylindrical; and
(b) said wick means is in the shape of a cylinder extending along the length of the walls of said chamber.

3. The apparatus of claim 1, further characterized by
(a) said anode is positioned at one end of said chamber;
(b) said cathode and said reference electrode are positioned at the end of said chamber opposite said anode; and
(c) said wick means extends between said anode at one end of said chamber and said cathode and reference electrode at the opposite end thereof.

4. The apparatus of claim 3, further characterized by
(a) said wick means has a plurality of folds therein.

* * * * *